United States Patent
Heuer et al.

(10) Patent No.: US 7,749,547 B2
(45) Date of Patent: Jul. 6, 2010

(54) NUTRITIONAL COMPOSITION AND METHOD FOR INCREASING CREATINE UPTAKE AND RETENTION IN SKELETAL MUSCLE, INCREASING MUSCLE MASS AND STRENGTH, INCREASING EXERCISE CAPACITY AND FOR AIDING RECOVERY FOLLOWING EXERCISE

(75) Inventors: Marvin A. Heuer, Mississauga (CA); Kenneth Clement, Mississauga (CA); Shan Chaudhuri, Mississauga (CA); James D. Ramsbottom, Mississauga (CA); Megan K. Thomas, Mississauga (CA)

(73) Assignee: New Cell Formulations Ltd., Ontario (CA)

( * ) Notice: Subject to any disclaimer, the term of this patent is extended or adjusted under 35 U.S.C. 154(b) by 91 days.

(21) Appl. No.: 11/522,266

(22) Filed: Sep. 14, 2006

(65) Prior Publication Data

US 2007/0196508 A1 Aug. 23, 2007

Related U.S. Application Data

(60) Provisional application No. 60/776,325, filed on Feb. 23, 2006.

(51) Int. Cl.
*A61K 36/605* (2006.01)
*A61K 31/375* (2006.01)
*A61K 36/00* (2006.01)

(52) U.S. Cl. .................. 424/725; 424/655; 514/474
(58) Field of Classification Search .................. None
See application file for complete search history.

(56) References Cited

U.S. PATENT DOCUMENTS

| | | | | |
|---|---|---|---|---|
| 5,520,932 | A * | 5/1996 | McCurdy et al. | 424/501 |
| 5,767,159 | A | 6/1998 | Hultman | |
| 5,968,544 | A | 10/1999 | Howard | |
| 5,968,900 | A | 10/1999 | Greenhaff | |
| 5,973,199 | A | 10/1999 | Negrisoli | |
| 6,136,339 | A | 10/2000 | Gardiner | |
| 6,616,936 | B1 * | 9/2003 | Martin et al. | 424/401 |
| 6,620,425 | B1 | 9/2003 | Gardiner | |
| 6,903,136 | B2 * | 6/2005 | Miller et al. | 514/556 |
| 6,946,151 | B2 * | 9/2005 | Chatterji | 424/725 |
| 2001/0041675 | A1 * | 11/2001 | Jacobs | 514/23 |
| 2004/0005368 | A1 * | 1/2004 | Mann et al. | 424/725 |
| 2004/0209801 | A1 | 10/2004 | Brand et al. | |
| 2005/0153001 | A1 * | 7/2005 | Aburdeineh et al. | 424/757 |
| 2005/0209148 | A1 * | 9/2005 | Rosenthal et al. | |
| 2005/0249843 | A1 * | 11/2005 | Wallis | 426/89 |
| 2007/0141119 | A1 * | 6/2007 | Zirzow et al. | |

FOREIGN PATENT DOCUMENTS

| | | | |
|---|---|---|---|
| CN | 1566313 A | * | 1/2005 |
| CN | 1568803 A | * | 1/2005 |
| IN | 200301028 | * | 6/2005 |
| IN | 2003010228 I3 | * | 6/2005 |
| JP | 07252148 A | * | 10/1995 |
| JP | 2002371003 | * | 12/2002 |
| JP | 2004217532 | * | 8/2004 |
| JP | 2004217532 A | * | 8/2004 |
| WO | WO 2006010560 | * | 2/2006 |
| WO | WO 2006010560 A | * | 2/2006 |

OTHER PUBLICATIONS

Latha et al., Effect of an aqueous extract of *Scoparia dulcis* on blood glucose, plasma insulin and some polyol pathway enzymes in experimental rat diabetes. Brazilian Journal of Medical and Biological Research 37: 577-586, 2004.*

Latha et al, Effect of an aqueous extract of *Scoparia dulcis* on blood glucose, plasma insulin and some polyol pathway enzymes in experimental rat diabetes, Brazilian Journal of Medical and Biological Research 37: 577-586, 2004.*

Anderson RA. Chromium in the prevention and control of diabetes. Diabetes Metab. Feb. 2000;26(1):22-7.

Arivazhagan et al., Effect of dl-alpha-lipoic acid on the status of lipid peroxidation and antioxidants in aged rats. Pharmacol Res. Mar. 2000;41(3):299-303.

Bahadori et al., Effect of chromium yeast and chromium picolinate on body composition of obese, non-diabetic patients during and after a formula diet. Acta Med Austriaca. 1997;24(5):185-7.

Bakker et al., Effect of taurine on sarcoplasmic reticulum function and force in skinned fast-twitch skeletal muscle fibres of the rat. J Physiol. Jan. 1, 2002;538(Pt 1):185-94.

Biolo et al., Physiologic hyperinsulinemia stimulates protein synthesis and enhances transport of selected amino acids in human skeletal muscle. J Clin Invest. Feb. 1995;95(2):811-9.

Biolo et al., Insulin action on muscle protein kinetics and amino acid transport during recovery after resistance exercise. Diabetes. May 1999;48(5):949-57.

Boirie et al. Differential insulin sensitivities of glucose, amino acid, and albumin metabolism in elderly men and women. J Clin Endocrinol Metab. Feb. 2001;86(2):638-44.

(Continued)

*Primary Examiner*—Michael V Meller
*Assistant Examiner*—Qiuwen Mi
(74) *Attorney, Agent, or Firm*—Fitzpatrick, Cella, Harper & Scinto

(57) ABSTRACT

A dietary supplement with Creatine, Taurine and a source of Phosphate. The dietary supplement may further include one or more of Double Fermented Triticum aestivum, Dextrose, Isomalt, Trehalose, D-Mannose, Mulberry extract, *Enicostemma littorale* Blume, *Scoparia dulcis*, Tarragon extract, *Andrographis paniculata*, Chromium, Glutamine and Alpha Lipoic Acid. Administered in the morning or following exercise, the dietary supplement increases Creatine uptake and retention in skeletal muscle, muscle mass and strength, exercise capacity and aids in recovery following exercise as well as supporting the immune system during periods of intense training.

20 Claims, No Drawings

OTHER PUBLICATIONS

Burke et al., Effect of alpha-lipoic acid combined with creatine monohydrate on human skeletal muscle creatine and phosphagen concentration. Int J Sport Nutr Exerc Metab. Sep. 2003;13(3):294-302.

Burke et al., The effect of continuous low dose creatine supplementation on force, power, and total work. Int J Sport Nutr Exerc Metab. Sep. 2000;10(3):235-44.

Caceres et al., Use of visual analogue scale measurements (VAS) to asses the effectiveness of standardized *Andrographis paniculata* extract SHA-10 in reducing the symptoms of common cold. A randomized double blind-placebo study. Phytomedicine. Oct. 1999;6(4):217-23).

Cade et al., Effects of phosphate loading on 2,3-diphosphoglycerate and maximal oxygen uptake. Med Sci Sports Exerc. Jun. 1984;16(3):263-8.

Casey et al., Metabolic response of type I and II muscle fibers during repeated bouts of maximal exercise in humans. Am J Physiol. Jul. 1996;271(1 Pt 1):E38-43.

Casey et al., Does dietary creatine supplementation play a role in skeletal muscle metabolism and performance? Am J Clin Nutr. Aug. 2000;72(2 Suppl):607S-17S.

Cuisinier et al., Role of taurine in osmoregulation during endurance exercise. Eur J Appl Physiol. Oct. 2002;87(6):489-95.

Doi et al., Studies on the constituents of the leaves of *Morus alba* L. Chem Pharm Bull (Tokyo). Feb. 2001;49(2):151-3.

Dunne et al., Ribose versus dextrose supplementation, association with rowing performance: a double-blind study. Clin J Sport Med. Jan. 2006;16(1):68-71.

Gaitanos et al., Human muscle metabolism during intermittent maximal exercise. J Appl Physiol. Aug. 1993;75(2):712-9.

Gostner et al., Effect of isomalt consumption on *Faecal microflora* and colonic metabolism in healthy volunteers. Br J Nutr. Jan. 2006;95(1):40-50.

Gostner et al., Effects of isomalt consumption on gastrointestinal and metabolic parameters in healthy volunteers. Br J Nutr. Oct. 2005;94(4):575-8.

Grant et al., Chromium and exercise training: effect on obese women. Med Sci Sports Exerc. Aug. 1997;29(8):992-8.

Green et al., Carbohydrate ingestion augments skeletal muscle creatine accumulation during creatine supplementation in humans. Am J Physiol. Nov. 1996;271(5 Pt 1):E821-6.

Greenhaff et al., Effect of oral creatine supplementation on skeletal muscle phosphocreatine resynthesis. Am J Physiol. May 1994;266(5 Pt 1):E725-30.

Greenhaff et al., Influence of oral creatine supplementation of muscle torque during repeated bouts of maximal voluntary exercise in man. Clin Sci (Lond). May 1993;84(5):565-71.

Hagen et al., (R)-alpha-lipoic acid-supplemented old rats have improved mitochondrial function, decreased oxidative damage, and increased metabolic rate. FASEB J. Feb. 1999;13(2):411-8.

Harris et al., Elevation of creatine in resting and exercised muscle of normal subjects by creatine supplementation. Clin Sci (Lond). Sep. 1992;83(3):367-74.

Hiscock et al., A comparison of plasma glutamine concentration in athletes from different sports. Med Sci Sports Exerc. Dec. 1998;30(12):1693-6.

Kalman et al., A Double-Blind Clinical Evaluation Comparing Two Popular Dietary Supplements Purported to Enhance Lean Body Mass. FASEB. 2000,14(4):A619.

Kalman et al., A double-blind, randomized clinical trial evaluating different creatine monohydrate formulations in resistance trained males. Med Sci Sports Exerc. 2000, 32(5), Supplement abstract 562.

Kang et al., Enhancement of neuroprotection of mulberry leaves (*Morus alba* L.) prepared by the anaerobic treatment against ischemic damage. Biol Pharm Bull. Feb. 2006;29(2):270-4.

Kapil et al., Antihepatotoxic effects of major diterpenoid constituents of *Andrographis paniculata*. Biochem Pharmacol. Jul. 6, 1993;46(1):182-5.

Khan et al., Insulin regulation of glucose uptake: a complex interplay of intracellular signalling pathways. Diabetologia. Nov. 2002;45(11):1475-83.

Kim et al., Anti-obesity effects of alpha-lipoic acid mediated by suppression of hypothalamic AMP-activated protein kinase. Nat Med. Jul. 2004;10(7):727-33.

Kreider et al. Effects of phosphate loading on oxygen uptake, ventilatory anaerobic threshold, and run performance. Med Sci Sports Exerc. Apr. 1990;22(2):250-6.

Lawler et al., Direct antioxidant properties of creatine. Biochem Biophys Res Commun. Jan. 11, 2002;290(1):47-52.

Lee et al., Obesity: the role of hypothalamic AMP-activated protein kinase in body weight regulation. Int J Biochem Cell Biol. Nov. 2005;37(11):2254-9.

Maroo et al., Glucose lowering effect of aqueous extract of *Enicostemma littorale* Blume in diabetes: a possible mechanism of action. J Ethnopharmacol. Aug. 2002;81(3):317-20.

Maroo et al., Dose dependent hypoglycemic effect of aqueous extract of *Enicostemma littorale* blume in alloxan induced diabetic rats. Phytomedicine. Mar. 2003;10(2-3):196-9.

Matsuzaki et al., Decreased taurine concentration in skeletal muscles after exercise for various durations. Med Sci Sports Exerc. May 2002;34(5):793-7).

Melchior et al., . Double-blind, placebo-controlled pilot and phase III study of activity of standardized *Andrographis paniculata* Herba Nees extract fixed combination (Kan jang) in the treatment of uncomplicated upper-respiratory tract infection. Phytomedicine. Oct. 2000;7(5):341-50.

Miyazaki et al., Optimal and effective oral dose of taurine to prolong exercise performance in rat. Amino Acids. Dec. 2004;27(3-4):291-8.

Musabayane et al., Effects of oral administration of some herbal extracts on food consumption and blood glucose levels in normal and streptozotocin-treated diabetic rats. Methods Find Exp Clin Pharmacol. May 2006;28(4):223-8).

Nakaya et al., Taurine improves insulin sensitivity in the Otsuka Long-Evans Tokushima Fatty rat, a model of spontaneous type 2 diabetes. Am J Clin Nutr. Jan. 2000;71(1):54-8).

Nandhini et al., Taurine modulates kallikrein activity and glucose metabolism in insulin resistant rats. Amino Acids. 2002;22(1):27-38).

Newsholme et al., Biochemical mechanisms to explain immunosuppression in well-trained and overtrained athletes. Int J Sports Med. Oct. 1994;15 Suppl 3:S142-7).

Odoom et al., regulation of total creatine content in a myoblast cell line. Mol Cell Biochem. May 24, 1996;158(2):179-88).

Oku et al., Inhibitory effects of extractives from leaves of *Morus alba* on human and rat small intestinal disaccharidase activity. Br J Nutr. May 2006;95(5):933-8).

Pari et al., Antihyperlipidemic effect of *Scoparia dulcis* (sweet broomweed) in streptozotocin diabetic rats. J Med Food. 2006 Spring;9(1):102-7).

Pari et al., Protective role of *Scoparia dulcis* plant extract on brain antioxidant status and lipidperoxidation in STZ diabetic male Wistar rats. BMC Complement Altern Med. Nov. 2, 2004;4:16).

Park et al., Cortisol and IGF-1 synergistically up-regulate taurine transport by the rat skeletal muscle cell line, L6. Biofactors. 2004;21(1-4):403-6).

Ramamoorthy et al., Functional characterization and chromosomal localization of a cloned taurine transporter from human placenta. Biochem J. Jun. 15, 1994;300 ( Pt 3):893-900).

Rave et al., Impact of a Diet with Balantose™ on Insulin Resistance, Lipids and Body Weight: Results of a Randomized, Controlled Cross-Over Study in Obese Subjects with High Risk for Type 2 Diabetes. 65th Annual Scientific Sessions, American Diabetes Association 2005, Abstract 1765-P.

Riales et al., Effect of chromium chloride supplementation on glucose tolerance and serum lipids including high-density lipoprotein of adult men. Am J Clin Nutr 1981;34:2670-8).

Ribnicky et al., Toxicological evaluation of the ethanolic extract of *Artemisia dracunculus* L. For use as a dietary supplement and in functional foods. Food Chem Toxicol. Apr. 2004;42(4):585-98.

Sayyah et al., Anticonvulsant activity and chemical composition of *Artemisia dracunculus* L. essential oil. J Ethnopharmacol. Oct. 2004;94(2-3):283-7).

Schaeffer et al., Mannose-sensitive adherence of *Escherichia coli* to epithelial cells from women with recurrent urinary tract infections. J Urol. May 1984;131(5):906-10).

Sestili et al., Creatine supplementation affords cytoprotection in oxidatively injured cultured mammalian cells via direct antioxidant activity. Free Radic Biol Med. Mar. 1, 2006;40(5):837-49).

Shabert et al., Glutamine-antioxidant supplementation increases body cell mass in AIDS patients with weight loss: a randomized, double-blind controlled trial. Nutrition. Nov.-Dec. 1999;15.

Tanizawa et al., Unregulated elevation of glutamate dehydrogenase activity induces glutamine-stimulated insulin secretion: identification and characterization of a GLUD1 gene mutation and insulin secretion studies with MIN6 cells overexpressing the mutant glutamate dehydrogenase. Diabetes. Mar. 2002;51(3):712-7).11-12):860-4.

Srinivasan et al., Effect of aqueous *Enicostemma littorale* Blume extract on key carbohydrate metabolic enzymes, lipid peroxides and antioxidants in alloxan-induced diabetic rats. J Pharm Pharmacol. Apr. 2005;57(4):497-503).

Steenge et al., Protein- and carbohydrate-induced augmentation of whole body creatine retention in humans. J Appl Physiol. Sep. 2000;89(3):1165-71).

Streeper et al., Differential effects of lipoic acid stereoisomers on glucose metabolism in insulin-resistant skeletal muscle. Am J Physiol. Jul. 1997;273(1 Pt 1):E185-91.

Tanaka et al., Trehalose alleviates polyglutamine-mediated pathology in a mouse model of Huntington disease. Nat Med. Feb. 2004;10(2):148-54).

Tarnopolsky et al., Creatine monohydrate supplementation enhances high-intensity exercise performance in males and females. Int J Sport Nutr Exerc Metab. Dec. 2000;10(4):452-63).

Tarnopolsky et al., Creatine-dextrose and protein-dextrose induce similar strength gains during training. Med Sci Sports Exerc. Dec. 2001;33(12):2044-52).

Uozumi et al., Myogenic differentiation induces taurine transporter in association with taurine-mediated cytoprotection in skeletal muscles. Biochem J. Mar. 15, 2006;394(Pt 3):699-706).

Vandenberghe et al., Long-term creatine intake is beneficial to muscle performance during resistance training. J Appl Physiol. Dec. 1997;83(6):2055-63.

Vasu et al., Hypolipidaemic and antioxidant effect of *Enicostemma littorale* Blume aqueous extract in cholesterol fed rats. J Ethnopharmacol. Oct. 3, 2005;101(1-3):277-82).

Vedavathy et al., Antipyretic activity of six indigenous medicinal plants of Tirumala Hills, Andhra Pradesh, India. J Ethnopharmacol. May-Jun. 1991;33(1-2):193-6).

Volek et al., Performance and muscle fiber adaptations to creatine supplementation and heavy resistance training. Med Sci Sports Exerc. Aug. 1999;31(8):1147-56).

Volpi et al., Insulin and Protein Metabolism. In: Handbook of Physiology, L. Jefferson and A. Cherrington editors. New York: Oxford, 2001, p. 735-757.

Walter et al., Creatine monohydrate in muscular dystrophies: A double-blind, placebo-controlled clinical study. Neurology. May 9, 2000;54(9):1848-50).

Wang et al., Insulin unmasks a COOH-terminal Glut4 epitope and increases glucose transport across T-tubules in skeletal muscle. J Cell Biol. Oct. 1996;135(2):415-30.

Warskulat et al., Taurine transporter knockout depletes muscle taurine levels and results in severe skeletal muscle impairment but leaves cardiac function uncompromised. FASEB J. Mar. 2004;18(3):577-9).

Wollin et al., Effects of a medium chain triglyceride oil mixture and alpha-lipoic acid diet on body composition, antioxidant status, and plasma lipid levels in the Golden Syrian hamster. J Nutr Biochem. Jul. 2004;15(7):402-10).

Yatabe et al., Effects of taurine administration in rat skeletal muscles on exercise. J Orthop Sci. 2003;8(3):415-9).

Zhang et al., Role of taurine supplementation to prevent exercise-induced oxidative stress in healthy young men. Amino Acids. Mar. 2004;26(2):203-7).

Zhang et al., Anti-diabetic property of ethanolic extract of *Andrographis paniculata* in streptozotocin-diabetic rats. Acta Pharmacol Sin. Dec. 2000;21(12):1157-64).

Zhang et al., Antihyperglycaemic and anti-oxidant properties of *Andrographis paniculata* in normal and diabetic rats. Clin Exp Pharmacol Physiol. May-Jun. 2000;27(5-6):358-63).

Ziegler et al., Treatment of symptomatic diabetic polyneuropathy with the antioxidant alpha-lipoic acid: a 7-month multicenter randomized controlled trial (ALADIN III Study). ALADIN III Study Group. Alpha-Lipoic Acid in Diabetic Neuropathy. Diabetes Care. Aug. 1999;22(8):1296-301).

* cited by examiner

NUTRITIONAL COMPOSITION AND METHOD FOR INCREASING CREATINE UPTAKE AND RETENTION IN SKELETAL MUSCLE, INCREASING MUSCLE MASS AND STRENGTH, INCREASING EXERCISE CAPACITY AND FOR AIDING RECOVERY FOLLOWING EXERCISE

RELATED APPLICATIONS

The application is related to and claims benefit of priority to U.S. Provisional Patent Application Ser. No. 60/776,325, entitled "Compositions and method for increasing bioavailability of compositions for performance improvement", filed Feb. 23, 2006, the disclosure of which is hereby fully incorporated by reference.

FIELD OF THE INVENTION

The present invention relates to the composition of a dietary supplement provided for increasing Creatine uptake and retention in skeletal muscle, increasing muscle mass and strength, increasing exercise capacity and aiding in recovery following exercise as well as providing support for the immune system during intense periods of exercise. Furthermore, a method for achieving the same by way of administration of the composition is presented.

SUMMARY OF THE INVENTION

The foregoing needs, and other needs and objectives which will become apparent in the following description, are achieved in the present invention which comprises a dietary composition and method for enhancing Creatine uptake and retention in skeletal muscle, increasing muscle mass and strength, increasing lean muscle mass, and supporting the immune system of an individual, e.g., a human or an animal, during intense training periods. According to an embodiment of the present invention, there are provided compositions and methods which minimize catabolism and promote muscle anabolism, particularly in response to exercise. For example the compositions and methods may allow an individual to increase muscle size, strength or endurance training as well as reduce recovery time and facilitate an increased training volume leading to the same.

According to an embodiment of the present invention, there are provided compositions and methods which comprise at least a combination of Creatine or derivatives thereof, Taurine or derivatives thereof and a source of Phosphate.

According to additional or alternative embodiments of the present invention, there are provided compositions and methods that further comprise at least one of Double Fermented *Triticum aestivum*, Dextrose, Isomalt, Trehalose, D-Mannose, an extract of Mulberry, *Enicostemma littorale* Blume, *Scoparia dulcis*, an extract of Tarragon, *Andrographis paniculata*, Chromium or derivatives thereof, Glutamine and Alpha Lipoic Acid.

DETAILED DESCRIPTION OF THE INVENTION

In the following description, for the purposes of explanation, numerous specific details are set forth in order to provide a thorough understanding of the present invention. It will be apparent, however, to one skilled in the art that the present invention may be practiced without one or more of these specific details.

The present invention, according to various embodiments thereof, is directed to a dietary supplement for increasing Creatine uptake and retention in skeletal muscle, increasing muscle mass and strength, increasing exercise capacity and aiding in post-exercise recovery as well as providing support for the immune system during intense exercise training periods. The present invention comprises at least a source of Creatine or derivative thereof, Taurine or derivative thereof and a source of Phosphate. According to various embodiments, the present invention may further comprise combinations of Double Fermented *Triticum aestivum*, Dextrose, Isomalt, Trehalose, D-Mannose, an extract of Mulberry, *Enicostemma littorale* Blume, *Scoparia dulcis*, an extract of Tarragon, *Andrographis paniculata*, Chromium or derivatives thereof, Glutamine and Alpha Lipoic Acid.

Definitions

As used herein, "Carbohydrate" refers to at least a source of carbohydrates such as, but not limited to, monosaccharides, disaccharides, oligosaccharides, polysaccharides or derivatives thereof.

As used herein, "Creatine" refers to the chemical N-methyl-N-guanyl Glycine, (CAS Registry No. 57-00-1), also known as, (alpha-methyl guanido) acetic acid, N-(aminoiminomethyl)-N-glycine, Methylglycocyamine, Methylguanidoacetic Acid, or N-Methyl-N-guanylglycine. Additionally, as used herein, "Creatine" also includes derivatives of Creatine such as esters, and amides, and salts, as well as other derivatives, including derivatives that become active upon metabolism. Furthermore, Creatinol (CAS Registry No. 6903-79-3), also known as Creatine-O-Phosphate, N-methyl-N-(beta-hydroxyethyl)guanidine O-Phosphate, Aplodan, or 2-(carbamimidoyl-methyl-amino)ethoxyphosphonic acid, is henceforth in this disclosure considered to be a Creatine derivative.

As used herein, "Phosphate" refers to at least a source of Phosphate ions such as, but not limited to, Dipotassium Phosphate, Disodium Phosphate, Magnesium Phosphate or derivatives thereof.

Carbohydrate ingestion is known to stimulate the secretion of insulin which in turn facilitates the uptake of glucose into skeletal muscle via glucose transporter 4 (GLUT4) translocation (Wang W, Hansen P A, Marshall B A, Holloszy J O, Mueckler M. Insulin unmasks a COOH-terminal Glut4 epitope and increases glucose transport across T-tubules in skeletal muscle. J Cell Biol. 1996 October; 135(2):415-30). Glucose is then converted to and stored as glycogen and triglycerides. Concomitant with this, insulin inhibits the release and synthesis of glucose (Khan A H, Pessin J E. Insulin regulation of glucose uptake: a complex interplay of intracellular signalling pathways. Diabetologia. 2002 November; 45(11):1475-83). Moreover, insulin also plays an important role in protein metabolism where it inhibits the breakdown of protein or proteolysis (Volpi E and Wolfe B. Insulin and Protein Metabolism. In: Handbook of Physiology, L. Jefferson and A. Cherrington editors. New York: Oxford, 2001, p. 735-757; Boirie Y, Gachon P, Cordat N, Ritz P, Beaufrere B. Differential insulin sensitivities of glucose, amino acid, and albumin metabolism in elderly men and women. J Clin Endocrinol Metab. 2001 February; 86(2):638-44). Furthermore, insulin promotes the uptake of amino acids into muscle and stimulates protein synthesis (Biolo G, Declan Fleming R Y, Wolfe R R. Physiologic hyperinsulinemia stimulates protein synthesis and enhances transport of selected amino acids in human skeletal muscle. J Clin Invest. 1995 February; 95(2):811-9), particularly following exercise (Biolo G, Williams B D, Fleming R Y, Wolfe R R. Insulin action on muscle protein kinetics and amino acid transport during recovery after resistance exercise. Diabetes. 1999 May; 48(5):949-57). Insulin has also been shown to stimulate Creatine uptake by muscle cells (Odoom J E, Kemp G J, Radda G K. regulation of total creatine content in a myoblast cell line. Mol Cell Biochem. 1996 May 24; 158(2):179-88). Alpha Lipoic Acid has been shown to have insulin-like properties, which further aid in the retention of Creatine. (Streeper R S, Henriksen E J, Jacob S, Hokama J Y, Fogt D L, Tritschler H J. Differential effects of lipoic acid stereoisomers on glucose metabolism in insulin-resistant skeletal muscle. Am J Physiol. 1997 July; 273(1 Pt 1):E185-91; Ziegler D, Hanefeld M, Ruhnau K J, Hasche H, Lobisch M, Schutte K, Kerum G, Malessa R. Treatment of symptomatic diabetic polyneuropathy with the antioxidant alpha-lipoic acid: a 7-month multi-center randomized controlled trial (ALADIN III Study). ALADIN III Study Group. Alpha-Lipoic Acid in Diabetic Neuropathy. Diabetes Care. 1999 August; 22(8):1296-301). Via the combination of Creatine with Alpha Lipoic Acid and a small amount of carbohydrate, Creatine retention as compared to Creatine and carbohydrate alone is significantly improved (Burke D G, Chilibeck P D, Parise G, Tarnopolsky M A, Candow D G. Effect of alpha-lipoic acid combined with creatine monohydrate on human skeletal muscle creatine and phosphagen concentration. Int J Sport Nutr Exerc Metab. 2003 September; 13(3):294-302). Therefore, it is deemed to be advantageous that, for the purposes of Creatine retention, the actions of insulin be enhanced. Furthermore, it may be advantageous to increase the activity and availability of Creatine in skeletal muscle.

Combinations comprising some of the aforementioned ingredients have been shown to offer further benefit to muscle building and increasing strength. In one clinical trial, 32 males were divided into four groups of eight subjects. Group 1 received a combination of Creatine/Dextrose/Taurine/Alpha Lipoic Acid, Group 2 received Creatine plus grape juice, Group 3 received Creatine plus water, and group 4 a placebo. At Day 28 of the experiment, Group 1 had demonstrated greater improvements in body composition and muscular endurance as compared to the other three groups (Kalman D S, Colker C M, Swain M A, Shi Q, Maharam L G. A double-blind, randomized clinical trial evaluating different creatine monohydrate formulations in resistance trained males. Med Sci Sports Exerc. 2000, 32(5), Supplement abstract 562). In a further study, Creatine/Dextrose/Alpha Lipoic Acid was found to provide improved results versus supplementation with whey protein alone in terms of muscle mass gain (Kalman D S, Colker C M, Swain M A, Antonio J. A Double-Blind Clinical Evaluation Comparing Two Popular Dietary Supplements Purported to Enhance Lean Body Mass. FASEB. 2000, 14(4):A619). In an eight week study which included diet and weight training, subjects consuming a combination comprising Creatine/Dextrose/Taurine/Ascorbic Acid/Chromium/Alpha Lipoic Acid/Phosphorus gained significantly more mass than subjects consuming Protein/Dextrose alone (Tarnopolsky M A, Parise G, Yardley N J, Ballantyne C S, Olatinji S, Phillips S M. Creatine-dextrose and protein-dextrose induce similar strength gains during training. Med Sci Sports Exerc. 2001 December; 33(12):2044-52).

Not wishing to be bound by theory, it is herein believed that the activity of insulin initiated by the ingestion of carbohydrates, such as Dextrose as comprised in the present invention, can be enhanced and sustained by insulin potentiators such as, including but not limited to, Taurine, Alpha Lipoic Acid, an extract of Mulberry, Chromium, Glutamine, *Enicostemma littorale* Blume, *Scoparia dulcis*, an extract of Tarragon and *Andrographis paniculata*. In another embodiment, the present invention may comprise one or more of Isomalt, Trehalose or D-Mannose to further potentiate the secretion or activity of insulin. The enhanced activity of insulin may facilitate increased uptake and retention of Creatine, as incorporated into the present invention, by skeletal muscle. Subsequently, the increase in Creatine retention may facilitate increased muscle growth, increased muscle endurance and reduced post-exercise recovery time by virtue of the biological role of Creatine. Furthermore, advantageously, the biological role of Creatine may be aided by ensuring adequate Phosphate availability by the addition of supplemental Phosphates.

Creatine

Creatine is a naturally occurring amino acid derived from the amino acids glycine, arginine, and methionine. Although it is found in meat and fish, it is also synthesized by humans. Creatine is predominantly used as a fuel source in muscle. About 65% of Creatine is stored in muscle as Phosphocreatine (Creatine bound to a Phosphate molecule) (Casey A, Constantin-Teodosiu D, Howell S, Hultman E, Greenhaff P L. Metabolic response of type I and II muscle fibers during repeated bouts of maximal exercise in humans. Am J Physiol. 1996 July; 271(1 Pt 1):E38-43). Muscular contractions are fueled by the dephosphorylation of adenosine triphosphate (ATP) to produce adenosine diphosphate (ADP) and without a mechanism to replenish ATP stores, the supply of ATP would be totally consumed in 1-2 seconds (Casey A, Greenhaff P L. Does dietary creatine supplementation play a role in skeletal muscle metabolism and performance? Am J Clin Nutr. 2000 August; 72(2 Suppl):607S-17S). Phosphocreatine serves as a major source of Phosphate from which ADP is regenerated to ATP. Six seconds following the commencement of exercise, muscular concentrations of Phosphocreatine drop by almost 50% (Gaitanos G C, Williams C, Boobis L H, Brooks S. Human muscle metabolism during intermittent maximal exercise. J Appl Physiol. 1993 August; 75(2):712-9).

Creatine supplementation has been shown to increase the concentration of Creatine in the muscle (Harris R C, Soderlund K, Hultman E. Elevation of creatine in resting and exercised muscle of normal subjects by creatine supplementation. Clin Sci (Lond). 1992 September; 83(3):367-74) and further said supplementation enables an increase in the resynthesis of Phosphocreatine (Greenhaff P L, Bodin K, Soderlund K, Hultman E. Effect of oral creatine supplementation on skeletal muscle phosphocreatine resynthesis. Am J Physiol. 1994 May; 266(5 Pt 1):E725-30) leading to a rapid replenishment of ATP within the first two minutes following the commencement of exercise.

In the early 1990's it was first clinically demonstrated that supplemental Creatine can improve strength and reduce fatigue (Greenhaff P L, Casey A, Short A H, Harris R, Soderlund K, Hultman E. Influence of oral creatine supplementation of muscle torque during repeated bouts of maximal voluntary exercise in man. Clin Sci (Lond). 1993 May; 84(5): 565-71). Resistance training with supplemented creatine experiments display a result of increased strength and fat-free mass over a placebo in sedentary females (Vandenberghe K, Goris M, Van Hecke P, Van Leemputte M, Vangerven L, Hespel P. Long-term creatine intake is beneficial to muscle performance during resistance training. J Appl Physiol. 1997 December; 83(6):2055-63) and in male football players (Vandenberghe K, Goris M, Van Hecke P, Van Leemputte M, Vangerven L, Hespel P. Long-term creatine intake is beneficial to muscle performance during resistance training. J Appl Physiol. 1997 December; 83(6):2055-63). In addition to increasing fat-free mass and strength, Creatine supplementation increases muscle fiber cross sectional area (Volek J S, Duncan N D, Mazzetti S A, Staron R S, Putukian M, Gomez A L, Pearson D R, Fink W J, Kraemer W J. Performance and muscle fiber adaptations to creatine supplementation and heavy resistance training. Med Sci Sports Exerc. 1999 August; 31(8):1147-56) thereby increasing muscle volume. High-intensity exercise performance of both males and females is also improved by supplemental Creatine (Tarnopolsky M A, MacLennan D P. Creatine monohydrate supplementation enhances high-intensity exercise performance in males and females. Int J Sport Nutr Exerc Metab. 2000 December; 10(4):452-63; Burke D G, Silver S, Holt L E, Smith Palmer T, Culligan C J, Chilibeck P D. The effect of continuous low dose creatine supplementation on force, power, and total work. Int J Sport Nutr Exerc Metab. 2000 September; 10(3):235-44). Creatine supplementation may also benefit individuals with muscle dystrophy disorders by reducing muscle loss (Walter M C, Lochmuller H, Reilich P, Klopstock T, Huber R, Hartard M, Hennig M, Pongratz D, Muller-Felber W. Creatine monohydrate in muscular dystrophies: A double-blind, placebo-controlled clinical study. Neurology. 2000 May 9; 54(9):1848-50).

Furthermore, there is evidence that Creatine may have antioxidant properties (Lawler J M, Barnes W S, Wu G, Song W, Demaree S. Direct antioxidant properties of creatine. Biochem Biophys Res Commun. 2002 Jan. 11; 290(1):47-52; Sestili P. Martinelli C, Bravi G, Piccoli G, Curci R, Battistelli M, Falcieri E, Agostini D, Gioacchini A M, Stocchi V. Creatine supplementation affords cytoprotection in oxidatively injured cultured mammalian cells via direct antioxidant activity. Free Radic Biol Med. 2006 Mar. 1; 40(5):837-49). The antioxidant activity of Creatine may additionally aid post-exercise muscle recovery.

Creatine retention has been shown to be markedly improved by the concomitant ingestion with carbohydrates, up to 60% better, which may further be related to increased insulin concentration (Green A L, Hultman E, Macdonald I A, Sewell D A, Greenhaff P L. Carbohydrate ingestion augments skeletal muscle creatine accumulation during creatine supplementation in humans. Am J Physiol. 1996 November; 271(5 Pt 1):E821-6). Furthermore, glucose and Creatine uptake by muscle cells has been shown to be stimulated by insulin (Odoom J E, Kemp G J, Radda G K. regulation of total creatine content in a myoblast cell line. Mol Cell Biochem. 1996 May 24; 158(2):179-88). Thus, the ingestion of Creatine combined with a source of carbohydrates is recommended to improve retention. It may also be beneficial to include a source of protein at the time of Creatine ingestion (Steenge G R, Simpson E J, Greenhaff P L. Protein- and carbohydrate-induced augmentation of whole body creatine retention in humans. J Appl Physiol. 2000 September; 89(3):1165-71).

U.S. Pat. No. 5,767,159 purports to describe a method for increasing muscle capacity and replenishing ATP by administering daily Creatine in healthy mammals. The amount of said Creatine is at least 0.2-0.4 g per kg body weight and not less than 15 g in a 70 kg mammal to be taken for at least 2 days but not more than 7 days. The Creatine is administered in solution which may further include other conventional nutrients such as lipids, carbohydrates, amino acids, electrolytes, trace elements and vitamins.

U.S. Pat. No. 5,968,544 purports to describe compositions containing Creatine for human consumption suitable for use in a drink or as dry powder stable for storage. The Creatine is provided in an acidic yogurt-based semi-liquid composition or forms an acidic solution when mixed with water.

U.S. Pat. No. 5,973,199 purports to describe compositions for water soluble Creatine salts usable in foods.

U.S. Pat. No. 5,968,900 purports to describe compositions and methods for increasing Creatine and glycogen concentration in muscle by increasing blood plasma insulin concentration. In one described embodiment, the compositions described are composed of Creatine or Creatine derivatives with a carbohydrate, wherein the carbohydrate is said to cause an increase in blood plasma insulin levels, which results in increases Creatine retention.

In an embodiment of the present invention, which is set forth in greater detail in the examples below, the dietary supplement includes Creatine or derivatives thereof. A serving of the dietary supplement may include from about 3 g to about 15 g of Creatine or derivatives thereof. The preferred dosage of a serving of the dietary supplement comprises about 10 g of Creatine or derivatives thereof.

Taurine

Taurine, an amino acid found primarily in nerve and muscle tissue, is generally considered to be a conditionally-essential amino acid, being only required under certain circumstances. As it is not utilized for protein synthesis, Taurine is found in the free form or in some small peptides. The accumulation of Taurine within cells is mediated via a high affinity sodium-dependent transporter (Ramamoorthy S, Leibach F H, Mahesh V B, Han H, Yang-Feng T, Blakely R D, Ganapathy V. Functional characterization and chromosomal localization of a cloned taurine transporter from human placenta. Biochem J. 1994 Jun. 15; 300 (Pt 3):893-900). The expression of this Taurine transporter is induced by differentiation program of myocytes (muscle cells) (Uozumi Y, Ito T, Hoshino Y, Mohri T, Maeda M, Takahashi K, Fujio Y, Azuma J. Myogenic differentiation induces taurine transporter in association with taurine-mediated cytoprotection in skeletal muscles. Biochem J. 2006 Mar. 15; 394(Pt 3):699-706). Exercise-induced hormones are also known to activate the Taurine transporter (Park S H, Lee H, Park T. Cortisol and IGF-1 synergistically up-regulate taurine transport by the rat skeletal muscle cell line, L6. Biofactors. 2004; 21(1-4):403-6). Moreover, genetically modified mice lacking the Taurine transporter have depleted Taurine levels in all muscle and have impaired skeletal muscle function (Warskulat U, Flogel U, Jacoby C, Hartwig H G, Thewissen M, Merx M W, Molojavyi A, Heller-Stilb B, Schrader J, Haussinger D. Taurine transporter knockout depletes muscle taurine levels and results in severe skeletal muscle impairment but leaves cardiac function uncompromised. FASEB J. 2004 March; 18(3): 577-9)

One of the main roles of Taurine is the regulation of fluid balance and is released by contracting muscles (Cuisinier C, Michotte De Welle J, Verbeeck R K, Poortmans J R, Ward R, Sturbois X, Francaux M. Role of taurine in osmoregulation during endurance exercise. Eur J Appl Physiol. 2002 October; 87(6):489-95). Taurine has also been shown to modulate the contractile function of mammalian skeletal muscle (Bakker A J, Berg H M. Effect of taurine on sarcoplasmic reticulum function and force in skinned fast-twitch skeletal muscle fibres of the rat. J Physiol. 2002 Jan. 1; 538(Pt 1):185-94). In rats, the Taurine concentration in muscle decreases as a result of exercise (Matsuzaki Y, Miyazaki T, Miyakawa S, Bouscarel B, Ikegami T, Tanaka N. Decreased taurine concentration in skeletal muscles after exercise for various durations. Med Sci Sports Exerc. 2002 May; 34(5):793-7) and oral supplementation with Taurine has been shown to maintain the concentration of Taurine in muscle and prolong exercise performance (Miyazaki T, Matsuzaki Y, Ikegami T, Miyakawa S, Doy M, Tanaka N, Bouscarel B. Optimal and effective oral dose of taurine to prolong exercise performance in rat. Amino Acids. 2004 December; 27(3-4):291-8; Yatabe Y, Miyakawa S, Miyazaki T, Matsuzaki Y, Ochiai N. Effects of taurine administration in rat skeletal muscles on exercise. J Orthop Sci. 2003; 8(3):415-9).

In a model of spontaneous diabetes, Taurine supplementation has been shown to improve insulin sensitivity in rats (Nakaya Y, Minami A, Harada N, Sakamoto S, Niwa Y, Ohnaka M. Taurine improves insulin sensitivity in the Otsuka Long-Evans Tokushima Fatty rat, a model of spontaneous type 2 diabetes. Am J Clin Nutr. 2000 January; 71(1):54-8). Furthermore, Taurine improves glucose metabolism in insulin resistant rats (Nandhini A T, Anuradha C V. Taurine modulates kallikrein activity and glucose metabolism in insulin resistant rats. Amino Acids. 2002; 22(1):27-38), suggesting that Taurine has insulin-like properties which may improve Creatine uptake and retention within muscle cells. Supplementation with Taurine has additionally been shown to reduce exercise-induced oxidative damage and enhance recovery (Zhang M, Izumi I, Kagamimori S, Sokejima S, Yamagami T, Liu Z, Qi B. Role of taurine supplementation to prevent exercise-induced oxidative stress in healthy young men. Amino Acids. 2004 March; 26(2):203-7).

In an embodiment of the present invention, which is set forth in greater detail in the examples below, the dietary supplement includes Taurine or derivatives thereof. A serving of the dietary supplement may include from about 0.5 g to about 3 g of Taurine or derivatives thereof. The preferred dosage of a serving of the dietary supplement comprises about 2.1 g of Taurine or derivatives thereof.

Phosphate

Phosphate, or phosphorus, is the second most abundant mineral in the body with calcium being the most abundant. As a Phosphate salt with calcium, Phosphate is involved in the formation of bone and teeth. In other salt complexes, Phosphate is involved in acid-base balance. Phosphate is also important for the structures of DNA and cell membranes. One of the most important roles of Phosphate is energy production in muscle as ATP and Phosphocreatine. Phosphate is also part of a compound in red blood cells known as 2,3 DPG (2,3-diphosphoglycerate), which facilitates the release of oxygen to the muscle tissues.

Supplemental Phosphate salts have been shown to increase the concentration of 2,3 DPG in red blood cells, increasing VO2 max (a measure of aerobic fitness) and a reduction in the production of lactate (Cade R, Conte M, Zauner C, Mars D, Peterson J, Lunne D, Hommen N, Packer D. Effects of phosphate loading on 2,3-diphosphoglycerate and maximal oxygen uptake. Med Sci Sports Exerc. 1984 June; 16(3):263-8). Moreover, Phosphate has also been shown to enhance oxygen uptake and run performance without affecting the level of 2,3 DPG (Kreider R B, Miller G W, Williams M H, Somma C T, Nasser T A. Effects of phosphate loading on oxygen uptake, ventilatory anaerobic threshold, and run performance. Med Sci Sports Exerc. 1990 April; 22(2):250-6).

The metabolic rate can also be increased by Phosphate supplementation (Nazar K, Kaciuba-Uscilko H, Szczepanik J, Zemba A W, Kruk B, Chwalbinska-Moneta J, Titow-Stupnicka E, Bicz B, Krotkiewski M. Phosphate supplementation prevents a decrease of triiodothyronine and increases resting metabolic rate during low energy diet. J Physiol Pharmacol. 1996 June; 47(2):373-83).

In an embodiment of the present invention, which is set forth in greater detail in the examples below, the dietary supplement includes a source of Phosphate or derivatives thereof. A serving of the dietary supplement may include from about 0.1 g to about 1.5 g of Phosphate or derivatives thereof. The preferred dosage of a serving of the dietary supplement comprises about 0.18 g of elemental Phosphate or derivatives thereof.

Alpha Lipoic Acid

Alpha Lipoic Acid (ALA) is an enzyme found in the cellular energy-producing structures, the mitochondria. ALA works in synergy with vitamins C and E as an antioxidant in both the water- and fat-soluble environments.

In rats supplemented with ALA, the negative age-related changes in mitochondrial function, accumulated oxidative damage and metabolic rate were all improved (Hagen T M, Ingersoll R T, Lykkesfeldt J, Liu J, Wehr C M, Vinarsky V, Bartholomew J C, Ames A B. (R)-alpha-lipoic acid-supplemented old rats have improved mitochondrial function, decreased oxidative damage, and increased metabolic rate. FASEB J. 1999 February; 13(2):411-8). As such, the antioxidant activity of ALA is likely involved in the prevention of cell death due to an improvement in oxidative stress (Arivazhagan P, Juliet P, Panneerselvam C. Effect of di-alpha-lipoic acid on the status of lipid peroxidation and antioxidants in aged rats. Pharmacol Res. 2000 March; 41(3):299-303). Furthermore, ALA has been linked to a beneficial increase in high-density lipoproteins (Wollin S D, Wang Y, Kubow S, Jones P J. Effects of a medium chain triglyceride oil mixture and alpha-lipoic acid diet on body composition, antioxidant status, and plasma lipid levels in the Golden Syrian hamster. J Nutr Biochem. 2004 July; 15(7):402-10) possibly due to its known effects as an antioxidant.

Additionally, ALA appears to possess a dual action related to hunger and β-oxidation of fat. First, the activity of AMP-activated protein kinase, which acts as an energy sensor in the hypothalamus, is reduced by ALA in rodents, this results in a profound weight loss by reducing food intake and enhancing energy expenditure (Kim M S, Park J Y, Namkoong C, Jang P G, Ryu J W, Song H S, Yun J Y, Namgoong I S, Ha J, Park I S, Lee I K, Viollet B, Youn J H, Lee H K, Lee K U. Anti-obesity effects of alpha-lipoic acid mediated by suppression of hypothalamic AMP-activated protein kinase. Nat Med. 2004 July; 10(7):727-33). Second, ALA increases Uncoupling Protein-1 in rodent adipocytes while increasing AMP-activated protein kinase in skeletal muscle cells and increasing glucose uptake and energy expenditure (Lee W J, Koh E H, Won J C, Kim M S, Park J Y, Lee K U. Obesity: the role of hypothalamic AMP-activated protein kinase in body weight regulation. Int J Biochem Cell Biol. 2005 November; 37(11):2254-9). Therefore, ALA seemingly has different effects in different tissues. However, in adipocytes or muscle cells ALA increases fatty acid oxidation, leading to an increase in energy expenditure and a decrease in weight and food intake.

U.S. Pat. Nos. 6,136,339 and 6,620,425 disclose compositions and methods for enhancing an athlete's muscle size or strength using a combination of Creatine, Alpha Lipoic Acid and optionally Dextrose, to be taken mixed with water daily following exercise.

In an embodiment of the present invention, which is set forth in greater detail in the examples below, the dietary supplement may include Alpha Lipoic Acid or derivatives thereof. A serving of the dietary supplement may include from about 0.005 g to about 0.4 g of Alpha Lipoic Acid or derivatives thereof. The preferred dosage of a serving of the dietary supplement comprises about 0.25 g of Alpha Lipoic Acid or derivatives thereof.

Dextrose

Dextrose is a simple sugar or monosaccharide commonly known as D-glucose. Also known as 'grape sugar' or 'blood sugar', it is found mainly in honey and fruits and is a building-block of glycogen, cellulose and starch. Recently, Dextrose was shown to boost the performance a female rowers as compared to ribose, which had been theorized to replenish muscle energy (Dunne L, Worley S, Macknin M. Ribose versus dextrose supplementation, association with rowing performance: a double-blind study. Clin J Sport Med. 2006 January; 16(1):68-71).

In an embodiment of the present invention, which is set forth in greater detail in the examples below, the dietary supplement may include Dextrose. A serving of the dietary supplement may include from about 50 g to about 100 g of Dextrose. The preferred dosage of a serving of the dietary supplement comprises about 75 g of Dextrose.

Mulberry Extract

Mulberry (*Morus alba*) is an edible plant used in Chinese medicine which is rich in flavonoids possessing antioxidant activity (Doi K, Kojima T, Makino M, Kimura Y, Fujimoto Y. Studies on the constituents of the leaves of *Morus alba* L. Chem Pharm Bull (Tokyo). 2001 February; 49(2):151-3). Orally administered mulberry extracts of Mulberry reduced blood glucose levels of both non-diabetic and streptozotocin-treated diabetic rats, commensurate with decreased food intake (Musabayane C T, Bwititi P T, Ojewole J A. Effects of oral administration of some herbal extracts on food consumption and blood glucose levels in normal and streptozotocin-treated diabetic rats. Methods Find Exp Clin Pharmacol. 2006 May; 28(4):223-8). Orally consumed extracts of Mulberry have also been shown to inhibit increases in blood glucose resulting from the ingestion of carbohydrates such as sucrose in humans and rats (Oku T, Yamada M, Nakamura M, Sadamori N, Nakamura S. Inhibitory effects of extractives from leaves of *Morus alba* on human and rat small intestinal disaccharidase activity. Br J Nutr. 2006 May; 95(5):933-8). Furthermore, extracts of Mulberry confer neuroprotective benefits (Kang T H, Oh H R, Jung S M, Ryu J H, Park M W, Park Y K, Kim S Y. Enhancement of neuroprotection of mulberry leaves (*Morus alba* L.) prepared by the anaerobic treatment against ischemic damage. Biol Pharm Bull. 2006 February; 29(2):270-4) and may further attenuate the development of atherosclerotic lesions (Enkhmaa B, Shiwaku K, Katsube T, Kitajima K, Anuurad E, Yamasaki M, Yamane Y. Mulberry (*Morus alba* L.) leaves and their major flavonol quercetin 3-(6-malonylglucoside) attenuate atherosclerotic lesion development in LDL receptor-deficient mice. J Nutr. 2005 April; 135(4):729-34).

In an embodiment of the present invention, which is set forth in greater detail in the examples below, the dietary supplement may include Mulberry extract. A serving of the dietary supplement may include from about 0.01 g to about 0.05 g of Mulberry extract. The preferred dosage of a serving of the dietary supplement comprises about 0.025 g of Mulberry extract.

Chromium

Chromium is an essential trace mineral that is used to control blood sugar levels by aiding insulin, which can help control or reduce weight. Chromium is poorly absorbed by the body and must therefore be combined with a more efficiently absorbed compound such as niacin as in the case of polynicotinate. Chromium likely exerts its main function as a component or a co-factor of the glucose tolerance factor, which is involved in insulin sensitivity.

Chromium has been shown clinically to increase lean mass (Bahadori B, Wallner S, Schneider H, Wascher T C, Toplak H. Effect of chromium yeast and chromium picolinate on body composition of obese, non-diabetic patients during and after a formula diet. Acta Med Austriaca. 1997; 24(5):185-7) and reduce body fat when combined with exercise (Grant K E, Chandler R M, Castle A L, Ivy J L. Chromium and exercise training: effect on obese women. Med Sci Sports Exerc. 1997 August; 29(8):992-8). Moreover, chromium has also been shown to increase high density lipoproteins (HDL i.e. 'good' cholesterol) (Riales R, Albrink M J. Effect of chromium chloride supplementation on glucose tolerance and serum lipids including high-density lipoprotein of adult men. Am J Clin Nutr 1981; 34:2670-8). Numerous clinical studies have demonstrated the relationship between supplemental Chromium and improved insulin activity and glucose metabolism (Anderson R A. Chromium in the prevention and control of diabetes. Diabetes Metab. 2000 February; 26(1):22-7).

In an embodiment of the present invention, which is set forth in greater detail in the examples below, the dietary supplement may include a derivative of Chromium. A serving of the dietary supplement may include from about 0.001 g to about 0.005 g of a derivative of Chromium. The preferred dosage of a serving of the dietary supplement comprises about 0.003 g of a derivative of Chromium.

Glutamine

Glutamine is the most abundant amino acid found in muscle and has important functions as a precursor for the synthesis of other amino acids. Many cells required for immune function rely on Glutamine as source for energy production.

Physical activity can deplete Glutamine levels, and as such, Glutamine is often considered to be a 'conditionally essential' amino acid. A study examining the Glutamine levels of groups involved in several different types of activities or sports found that powerlifters and swimmers had lower Glutamine levels than cyclists and non-athletes (Hiscock N, Mackinnon L T. A comparison of plasma glutamine concentration in athletes from different sports. Med Sci Sports Exerc. 1998 December; 30(12):1693-6), suggesting that high resistance load activities require increased amounts of Glutamine. Moreover, this depletion of Glutamine has been linked to immunosuppression often resulting from intense training (Newsholme E A. Biochemical mechanisms to explain immunosuppression in well-trained and overtrained athletes. Int J Sports Med. 1994 October; 15 Suppl 3:S142-7). Supplementation with Glutamine in conjunction with additional antioxidants can increase body weight, body cell mass, and intracellular water when compared with placebo (Shabert J K, Winslow C, Lacey J M, Wilmore D W. Glutamine-antioxidant supplementation increases body cell mass in AIDS patients with weight loss: a randomized, double-blind controlled trial. Nutrition. 1999 November-December; 15(11-12):8604). Glutamine is also capable of stimulating insulin secretion (Tanizawa Y, Nakai K, Sasaki T, Anno T, Ohta Y, Inoue H, Matsuo K, Koga M, Furukawa S, Oka Y. Unregulated elevation of glutamate dehydrogenase activity induces glutamine-stimulated insulin secretion: identification and characterization of a GLUD1 gene mutation and insulin secretion studies with MIN6 cells overexpressing the mutant glutamate dehydrogenase. Diabetes. 2002 March; 51 (3):712-7).

In an embodiment of the present invention, which is set forth in greater detail in the examples below, the dietary supplement may include Glutamine or a derivative thereof. A serving of the dietary supplement may include from about 0.001 g to about 0.005 g of Glutamine or a derivative thereof. The preferred dosage of a serving of the dietary supplement comprises about 0.002 g of Glutamine or a derivative thereof.

*Enicostemma littorale* Blume

*Enicostemma littorale* Blume is a flower-producing herb found in South America, Africa, and Asia. In rat models of diabetes, *Enicostemma littorale* extract can enhance glucose-induced insulin release thereby effectively lowering blood glucose levels (Maroo J, Vasu V T, Aalinkeel R, Gupta S. Glucose lowering effect of aqueous extract of *Enicostemma littorale* Blume in diabetes: a possible mechanism of action. J Ethnopharmacol. 2002 August; 81(3):317-20; Maroo J, Vasu V T, Gupta S. Dose dependent hypoglycemic effect of aqueous extract of *Enicostemma littorale* blume in alloxan induced diabetic rats. Phytomedicine. 2003 March; 10(2-3): 196-9). Furthermore, *Enicostemma littorale* extract counters the changes in several metabolic enzymes and antioxidants observed in diabetic rats, including lowering thiobarbituric acid reactive substances and lipid hydroperoxides while increasing the concentration of reduced glutathione and the activities of superoxide dismutase and catalase (Srinivasan M, Padmanabhan M, Prince P S. Effect of aqueous *Enicostemma littorale* Blume extract on key carbohydrate metabolic enzymes, lipid peroxides and antioxidants in alloxan-induced diabetic rats. J Pharm Pharmacol. 2005 April; 57(4): 497-503). The lipid profile of rats fed cholesterol was also improved by administration of *Enicostemma littorale* extract (Vasu V T, Modi H, Thaikoottathil J V, Gupta S. Hypolipidaemic and antioxidant effect of *Enicostemma littorale* Blume aqueous extract in cholesterol fed rats. J Ethnopharmacol. 2005 Oct. 3; 101(1-3):277-82).

In an embodiment of the present invention, which is set forth in greater detail in the examples below, the dietary supplement may include *Enicostemma littorale* Blume. A serving of the dietary supplement may include from about 0.0005 g to about 0.003 g of *Enicostemma littorale* Blume. The preferred dosage of a serving of the dietary supplement comprises about 0.001 g of *Enicostemma littorale* Blume.

*Scoparia dulcis* (Scotch Brum)

*Scoparia dulcis* is a tropical herb found in abundance in South America and the Amazon rainforest and has been used traditionally for multiple treatments including diabetes. Extracts of *Scoparia dulcis* provide both antidiabetic and antihyperlipidemic actions in normal and experimentally diabetic rats (Pari L, Latha M. Antihyperlipidemic effect of *Scoparia dulcis* (sweet broomweed) in streptozotocin diabetic rats. J Med Food. 2006 Spring; 9(1):102-7). *Scoparia dulcis* extract has also demonstrated antioxidant and neuroprotective activity (Pari L, Latha M. Protective role of *Scoparia dulcis* plant extract on brain antioxidant status and lipidperoxidation in STZ diabetic male Wistar rats. BMC Complement Altern Med. 2004 Nov. 2; 4:16).

In an embodiment of the present invention, which is set forth in greater detail in the examples below, the dietary supplement may include *Scoparia dulcis*. A serving of the dietary supplement may include from about 0.0005 g to about 0.003 g of *Scoparia dulcis*. The preferred dosage of a serving of the dietary supplement comprises about 0.001 g of *Scoparia dulcis*.

Tarragon Extract (*Artemisia dracunculus*)

Russian Tarragon (*Artemisia dracunculus*) is a perennial herb widely used in cooking. Historically, it has been used as a natural blood cleanser and as a treatment for headaches and dizziness. Current studies are examining the use of an ethanolic extract of Russian Tarragon for the treatment of hyperglycemia associated with diabetes. The toxicology of this extract has been evaluated, and has been shown to be safe and non-toxic (Ribnicky D M, Poulev A, O'Neal J, Wnorowski G, Malek D E, Jager R, Raskin I. Toxicological evaluation of the ethanolic extract of *Artemisia dracunculus* L. for use as a dietary supplement and in functional foods. Food Chem Toxicol. 2004 April; 42(4):585-98). Essential oil extracted from *Artemisia dracunculus* may also have potential as an anticonvulsant and as a mild sedative (Sayyah M, Nadjafnia L, Kamalinejad M. Anticonvulsant activity and chemical composition of *Artemisia dracunculus* L. essential oil. J Ethnopharmacol. 2004 October; 94(2-3):283-7).

In an embodiment of the present invention, which is set forth in greater detail in the examples below, the dietary supplement may include Tarragon extract. A serving of the dietary supplement may include from about 0.0005 g to about 0.003 g of Tarragon extract. The preferred dosage of a serving of the dietary supplement comprises about 0.001 g of Tarragon extract.

*Andrographis paniculata*

*Andrographis paniculata* is a medicinal herb used traditionally throughout Asia used to treat a number of conditions. Clinical studies have demonstrated an immunity-enhancing benefit of *Andrographis paniculata* supplementation by reducing the occurrence and severity of common cold symptoms (Caceres D D, Hancke J L, Burgos R A, Sandberg F, Wikman G K. Use of visual analogue scale measurements (VAS) to asses the effectiveness of standardized *Andrographis paniculata* extract SHA-10 in reducing the symptoms of common cold. A randomized double blind-placebo study. Phytomedicine. 1999 October; 6(4):217-23) and upper-respiratory tract infections (Melchior J, Spasov A A, Ostrovskij O V, Bulanov A E, Wikman G. Double-blind, placebo-controlled pilot and phase III study of activity of standardized *Andrographis paniculata* Herba Nees extract fixed combination (Kan jang) in the treatment of uncomplicated upper-respiratory tract infection. Phytomedicine. 2000 October; 7(5):341-50). Additionally, *Andrographis paniculata* has been shown to possess antipyretic, fever-reducing, activity similar to that of aspirin (Vedavathy S, Rao K N. Antipyretic activity of six indigenous medicinal plants of Tirumala Hills, Andhra Pradesh, India. J Ethnopharmacol. 1991 May-June; 33(1-2):193-6). Furthermore, *Andrographis paniculata* has been shown to reduce chemically-induced liver toxicity in experimental mice (Kapil A, Koul I B, Banerjee S K, Gupta B D. Antihepatotoxic effects of major diterpenoid constituents of *Andrographis paniculata*. Biochem Pharmacol. 1993 Jul. 6; 46(1):182-5).

*Andrographis paniculata* extract possesses antihyperglycemic and antioxidative activities in both normal and chemically-induced diabetic rats (Zhang X F, Tan B K. Antihyperglycaemic and anti-oxidant properties of *Andrographis paniculata* in normal and diabetic rats. Clin Exp Pharmacol Physiol. 2000 May-June; 27(5-6):358-63). The antidiabetic properties of *Andrographis paniculata* are believed to be due at least in part to enhanced glucose metabolism (Zhang X F, Tan B K. Anti-diabetic property of ethanolic extract of *Andrographis paniculata* in streptozotocin-diabetic rats. Acta Pharmacol Sin. 2000 December; 21(12):1157-64).

In an embodiment of the present invention, which is set forth in greater detail in the examples below, the dietary supplement may include *Andrographis paniculata*. A serving of the dietary supplement may include from about 0.0005 g to about 0.003 g of *Andrographis paniculata*. The preferred dosage of a serving of the dietary supplement comprises about 0.001 g of *Andrographis paniculata*.

Double Fermented *Triticum aestivum*

Double Fermented *Triticum aestivum* is a whole-grain wheat product low in simple sugars and high in complex carbohydrates. This produces a more level glucose/insulin response rather than the typical 'spike' resulting from simple sugar ingestion. As such, Double Fermented *Triticum aestivum* is marketed towards overweight or obese individual or individuals with impaired glucose tolerance. Double Fermented *Triticum aestivum* was found effective at reducing the risks associated with development of type 2 diabetes such as elevated fasting blood glucose levels and obesity (Rave K, Dellweg S, Hovelmann U, Heise T, Dieck H T. Impact of a Diet with Balantose™ on Insulin Resistance, Lipids and Body Weight: Results of a Randomized, Controlled Cross-Over Study in Obese Subjects with High Risk for Type 2 Diabetes. 65th Annual Scientific Sessions, American Diabetes Association 2005, Abstract 1765-P).

In an embodiment of the present invention, which is set forth in greater detail in the examples below, the dietary supplement may include Double Fermented *Triticum aestivum*. A serving of the dietary supplement may include from about 0.05 g to about 0.3 g of Double Fermented *Triticum aestivum*. The preferred dosage of a serving of the dietary supplement comprises about 0.1 g of Double Fermented *Triticum aestivum*.

Isomalt

Isomalt is a disaccharide sugar substitute derived from sucrose which is less sweet than, and is often mixed with, more conventional sweeteners. Being only partially digested in the intestines, isomalt results in a low blood glucose effect, has benefits similar to that of dietary fiber, and has a caloric value of about half that of sugar. Moreover, Isomalt has been shown to promote healthy bowel function without impairing metabolic function (Gostner A, Schaffer V, Theis S, Menzel T, Luhrs H, Melcher R, Schauber J, Kudlich T, Dusel G, Dorbath D, Kozianowski G, Scheppach W. Effects of isomalt consumption on gastrointestinal and metabolic parameters in healthy volunteers. Br J Nutr. 2005 October; 94(4):575-81; Gostner A, Blaut M, Schaffer V, Kozianowski G, Theis S, Klingeberg M, Dombrowski Y, Martin D, Ehrhardt S, Taras D, Schwiertz A, Kleessen B, Luhrs H, Schauber J, Dorbath D, Menzel T, Scheppach W. Effect of isomalt consumption on faecal microflora and colonic metabolism in healthy volunteers. Br J Nutr. 2006 January; 95(1):40-50).

In an embodiment of the present invention, which is set forth in greater detail in the examples below, the dietary supplement may include Isomalt. A serving of the dietary supplement may include from about 0.0005 g to about 0.003 g of Isomalt. The preferred dosage of a serving of the dietary supplement comprises about 0.001 g of Isomalt.

Trehalose

Trehalose is a naturally occurring disaccharide found in plants, invertebrates and fungi and is about half as sweet as sucrose or table sugar. Trehalose has been discovered to be able to inhibit the aggregation of some proteins and thus has potential in the prevention of diseases linked to such events such as Huntington's disease (Tanaka M, Machida Y, Niu S, Ikeda T, Jana N R, Doi H, Kurosawa M, Nekooki M, Nukina N. Trehalose alleviates polyglutamine-mediated pathology in a mouse model of Huntington disease. Nat Med. 2004 February; 10(2):148-54).

In an embodiment of the present invention, which is set forth in greater detail in the examples below, the dietary supplement may include Trehalose. A serving of the dietary supplement may include from about 0.0005 g to about 0.003 g of Trehalose. The preferred dosage of a serving of the dietary supplement comprises about 0.001 g of Trehalose.

D-Mannose

Mannose is a monosaccharide found in some fruits including cranberry. It is absorbed slowly in the gastrointestinal tract, with most being excreted in the urine. D-mannose has been theorized to aid in the treatment of urinary tract infections by virtue of being able to bind to the surface proteins of infection-causing bacteria, thereby facilitating their clearance (Schaeffer A J, Chmiel J S, Duncan J L, Falkowski W S. Mannose-sensitive adherence of *Escherichia coli* to epithelial cells from women with recurrent urinary tract infections. J Urol. 1984 May; 131(5):906-10).

In an embodiment of the present invention, which is set forth in greater detail in the examples below, the dietary supplement may include D-mannose. A serving of the dietary supplement may include from about 0.0005 g to about 0.003 g of D-mannose. The preferred dosage of a serving of the dietary supplement comprises about 0.001 g of D-mannose.

According to various embodiments of the present invention, the dietary supplement may be consumed in any form. For instance, the dosage form of the dietary supplement may be provided as, e.g., a powder beverage mix, a liquid beverage, a ready-to-eat bar or drink product, a capsule, a liquid capsule, a tablet, a caplet, or as a dietary gel. The preferred dosage forms of the present invention is as a powder beverage mix or a drink product.

Fine-milling of Active Constituents

As set forth above, the dosage form of the dietary supplement, in accordance with the example embodiments set forth below, may be provided in accordance with customary processing techniques for herbal and/or dietary supplements, wherein the active ingredients are suitably processed into a desired form. In accordance with various embodiments of the present invention, one or more ingredients of the diet supplement are processed so as to form fine-milled particles. For instance, in various embodiments, one or more ingredients of the dietary supplemental are processed by a large-scale dry milling technique that produces fine particles, preferably known as fine-milled particles. The use of dry milling techniques, in combination with excipients and polymers, to form fine-milled particles has been shown to improve flow and dispersability, stability, resistance to moisture, bioavailability, and dissolution/release properties. Formulations benefit by containing fine-milled particles for the purpose of providing the one or more ingredients in particle sizes that optimize one or more of the flow and dispersability, stability, resistance to moisture, bioavailability, and dissolution/release properties of the one or more ingredients in a dietary supplement. In vitro tests designed to simulate the environment of a stomach were performed to test the dissolution rate of fine-milled particle tablets versus non-fine-milled. These test showed that in tablets produced from fine-milled particles the time to 100% dissolution was approximately 15 minutes. In the case of non-fine-milled particle compositions, only 90% dissolution was observed after 120 minutes. In preferred embodiments, the dietary supplemental contains fine-milled particles having an average size between about 50 nm and about 2 nm.

U.S. Provisional Patent Application 60/776,325 discloses a method for improving the absorption, palatability, taste, texture, and bioavailability of compounds by increasing the solubility of said compounds in proprietary formulations for the purposes of enhancing or improving muscle size, growth and/or recovery time and/or weight loss. The increased bioavailability of the compound or ingredients is achieved by reducing the particle size via "fine-milling" thereby increasing the surface area-to-volume ratio each particle, thus increasing the rate of dissolution. The compositions and methods disclosed promote increased bioavailability by increasing the total surface area of poorly soluble particles, thereby increasing the rate of absorption.

As used herein the, term "fine-milled" and/or "fine-milling" refers to the process of micronization. Micronization is a mechanical process that involves the application of force to a particle, thereby resulting in a reduction in the size of the particle. The force, in the case of micronization, may be applied in any manner such as, e.g., the collision of particles at high rates of speed, grinding, or by an air-jet micronizer. In preferred embodiments, fine-milled particles are obtained by jet-milling with nitrogen and compressed air.

As used herein, the term "particle size" refers to the diameter of the particle. The term "average particle size" means that at least 50% of the particles in a sample will have the specified particle size. Preferably, at least 80% of the particles in a sample will have the specified particle size, and more preferably, at least 90% of the particles in a given sample will have the specified particle size.

The size of a particle can be determined by any of the methods known within the art. Methods for particle size determination which may be employed are for example, e.g., sieves, sedimentation, electrozone sensing (Coulter counter), microscopy, and/or Low Angle Laser Light Scattering. The preferred methods for the particle size determination of the present invention are those methods which are most commonly used in the pharmaceutical industry, such as laser diffraction, e.g., via light scattering Coulter Delsa 440SX.

The fine-milling process may be employed in the processing of one or more of the ingredients of the present invention in the dosage forms of tablets, e.g., immediate-release film coated, modified-release and fast-dissolving; capsules or tablets, e.g., immediate-release and modified-release; liquid dispersions; powders; drink mixes, etc.

Preferably, the dietary supplement of the present invention is consumed by an individual in accordance with the following method: As a dietary supplement, a serving of said dietary supplement may be taken by means of mixing in about 360-450 ml of an acceptable aqueous fluid at least one (1) time daily wherein each serving is comprised of two (2) scoops comprising about 100 g total mass of the dietary supplement. Said dietary supplement may be consumed approximately 0 to 60 minutes following a workout, or in the morning upon waking on non-workout days. In this manner, the dietary supplement may increase Creatine uptake and retention in skeletal muscle, increase muscle mass and strength, increase exercise capacity and aid in post-exercise recovery as well as provide support for the immune system during intense exercise training periods.

Furthermore, the dosage form of the supplemental composition may be provided in accordance with customary processing techniques for herbal and dietary supplements in any of the forms mentioned above. Additionally, the dietary supplement set forth in the example embodiments herein may contain any appropriate number and type of excipients, as is well-known in the art.

The present dietary supplement or those similarly envisioned by one of skill in the art, may be utilized in compositions and methods for increasing Creatine uptake and retention in skeletal muscle, increasing muscle mass and strength, increasing exercise capacity and aiding in post-exercise recovery as well as providing support for the immune system during intense exercise training periods of an individual, e.g. a human or an animal in a formulation designed to be consumed at least one time per day.

Although the following examples illustrate the practice of the present invention in three of its various embodiments, the examples should not be construed as limiting the scope of the invention. Other embodiments will be apparent to one skilled in the art from consideration of the specification and example.

EXAMPLE 1

A serving of the dietary supplement comprises the following ingredients in powdered beverage mix form. The dietary supplement comprises for example: about 74 g of pharma grade Dextrose 99 DE, about 9 g of Creatine monohydrate, finely ground or milled, about 2.1 g of Taurine, about 0.33 g of Dipotassium Phosphate, about 0.33 g of Magnesium Phosphate, about 0.26 g of Sodium Alpha Lipoic Acid, about 0.025 g of and extract of Mulberry, about 0.003 g of Chromium polynicotinate, about 0.001 g of Anhydrous Creatine, about 0.001 g of Taurine ethyl ester HCl, about 0.001 g of Glutamine AKG 2:1, about 0.001 g of Glutamine ethyl ester HCl, about 0.001 g of *Enicostemma littorale* Blume, about 0.001 g of *Scoparia dulcis*, about 0.001 g of an extract of Tarragon, about 0.001 g of *Andrographis paniculata*.

Directions: As a dietary supplement, 2 scoops, comprising about 100 g total mass of the dietary supplement are administered by a means of mixing said dietary supplement in 360-450 ml of an acceptable aqueous fluid at least one (1) time daily. Said serving is to be consumed approximately 0 to 60 minutes following a workout or in the morning upon waking on non-workout days.

EXAMPLE 2

A serving of the dietary supplement comprises the following ingredients in powdered beverage mix form. The dietary supplement comprises for example: about 75 g of pharma grade Dextrose 99 DE, about 9 g of finely ground Creatine monohydrate, about 2.1 g of Taurine, about 1 g of fine-milled Creatine monohydrate, about 0.33 g of Dipotassium Phosphate, about 0.33 g of Disodium Phosphate, about 0.26 g of the Sodium salt of Alpha Lipoic Acid, about 0.025 g of an extract of Mulberry, about 0.003 g of Chromium polynicotinate, about 0.001 of Anhydrous Creatine, about 0.001 g of Dicreatine malate, about 0.001 g of Creatine HCA salt, about 0.001 g of Taurine ethyl ester HCl, about 0.001 g of Glutamine AKG 2:1, about 0.001 g of Glutamine ethyl ester HCl, about 0.001 g of *Enicostemma littorale* Blume, about 0.001 g of *Scoparia dulcis*, about 0.001 g of an extract of Tarragon extract, and about 0.001 g of *Andrographis paniculata*.

Directions: As a dietary supplement, 2 scoops, comprising about 100 g total mass of the dietary supplement are administered by a means of mixing said dietary supplement in 360-450 ml of an acceptable aqueous fluid at least one (1) time daily. Said serving is to be consumed approximately 0 to 60 minutes following a workout or in the morning upon waking on non-workout days.

EXAMPLE 3

A serving of the dietary supplement comprises the following ingredients in powdered beverage mix form. The dietary supplement comprises for example: about 75 g of pharma grade Dextrose 99 DE, about 9 g of finely ground Creatine monohydrate, about 2.1 g of Taurine, about 1 g of fine-milled Creatine monohydrate, about 0.33 g of Dipotassium Phosphate, about 0.33 g of Disodium Phosphate, about 0.33 g of Magnesium Phosphate, about 0.26 g of Sodium Alpha Lipoic Acid, about 0.1 g of Double Fermented *Triticum aestivum*, about 0.025 g of an extract of Mulberry, about 0.003 g of Chromium polynicotinate, about 0.001 g of Anhydrous Creatine, about 0.001 g of Creatine Dicreatine malate, about 0.001 g of Creatine pyroglutamate, about 0.001 g of Creatine HCA salt, about 0.001 g of Taurine ethyl ester HCl, about 0.001 g of Glutamine AKG 2:1, about 0.001 g of Glutamine ethyl ester HCl, about 0.001 g of *Enicostemma littorale* Blume, about 0.001 g of *Scoparia dulcis*, about 0.001 g of and extract of Tarragon, about 0.001 g of *Andrographis paniculata*, about 0.001 g of Isomalt, about 0.001 g of Trehalose, about 0.001 g of D-mannose.

Directions: As a dietary supplement, 2 scoops, comprising about 100 g total mass of the dietary supplement are administered by a means of mixing said dietary supplement in 360-450 ml of an acceptable aqueous fluid at least one (1) time daily. Said serving is to be consumed approximately 0 to 60 minutes following a workout or in the morning upon waking on non-workout days.

In the foregoing specification, the invention has been described with specific embodiments thereof, however, it will be evident that various modifications and changes may be made thereto without departing from the broader spirit and scope of the invention.

What is claimed:

1. A dietary supplement comprising an admixture of:
   Creatine or an ester, amide or salt thereof, or Creatinol-O-Phosphate;
   Taurine;
   *Andrographis paniculata;*
   creatine pyroglutamate;
   creatine hydroxycitric acid salt;
   Dipotassium Phosphate, Disodium Phosphate or Magnesium Phosphate; and
   a source of carbohydrates.

2. The dietary supplement of claim 1, further comprising at least two components selected from the group consisting of an extract of Mulberry, *Enicostemma littorale* Blume, *Scoparia dulcis*, extract of Tarragon, Alpha Lipoic Acid and Chromium.

3. The dietary supplement of claim 1, further comprising Glutamine.

4. The dietary supplement of claim 1, wherein the source of carbohydrates comprises at least one of monosaccharides, disaccharides, oligosaccharides, or polysaccharides.

5. The dietary supplement of claim 4, wherein the source of carbohydrates comprises dextrose.

6. The dietary supplement of claim 1, further comprising double fermented *Triticum aestivum*.

7. The dietary supplement of claim 1, further comprising ascorbic acid.

8. The dietary supplement of claim 1, further comprising Trehalose.

9. The dietary supplement of claim 1, wherein Creatine or an ester, amide or salt thereof, or Creatinol-O-Phosphate is present in an amount of about 3-15 grams; Taurine is present in an amount of about 0.5-3 grams; *Andrographis paniculata* is present in an amount of about 0.0005-0.003 grams; Dipotassium Phosphate, Disodium Phosphate or Magnesium Phosphate is present in an amount of about 0.1-1.5 grams; and the source of carbohydrate is dextrose present in an amount of from about 50 to about 100 grams.

10. The dietary supplement of claim 9, further comprising about 0.0005-0.003 grams Trehalose.

11. The dietary supplement of claim 9, further comprising about 0.001 g creatine pyroglutamate and about 0.001 g creatine hydroxycitric acid salt.

12. The dietary supplement of claim 10, further comprising about 0.001 g creatine pyroglutamate and about 0.001 g creatine hydroxycitric acid salt.

13. The dietary supplement of claim 2, comprising Alpha Lipoic Acid or extract of Mulberry.

14. The dietary supplement of claim 3, comprising Alpha Lipoic Acid or extract of Mulberry.

15. A dietary supplement comprising an admixture of:
    about 10 g of Creatine or an ester, amide or salt thereof, or Creatinol-O-Phosphate;
    about 2.1 g of Taurine;
    about 0.5 g of Dipotassium Phosphate, Disodium Phosphate or Magnesium Phosphate;
    about 82 g of Dextrose;
    about 0.001 g of Trehalose;
    about 0.025 g of an extract of Mulberry;
    about 0.001 g of *Eniscostemma littorale* Blume;
    about 0.001 g of creatine pyroglutamate;
    about 0.001 g of creatine hydroxycitric acid salt;
    about 0.001 g of *Scoparia dulcis;*
    about 0.001 g of an extract of Tarragon;
    about 0.001 g of *Andrographis paniculata;*
    about 0.003 g of Chromium Polynicotinate;
    about 0.002 g of Glutamine; and
    about 0.25 g of Alpha Lipoic Acid.

16. The dietary supplement of any one of claims 1, 2, 3 or 15, 13, 14, wherein at least a portion of said admixture is fine-milled to have an average particle size between 2-50 nm.

17. The dietary supplement of claim 15, further comprising about 0.1 g double fermented *Triticum aestivum*.

18. A method of supplementing the diet of an individual comprising a step of administering to an individual a dietary supplement according to any one of claims 1, 2, 3, 13-15, 4-7, 8, or 9-12.

19. The method of claim 18, wherein the dietary supplement is administered to said individual 0-60 minutes following a workout.

20. The method of claim 18, wherein the dietary supplement is administered to said individual upon waking on non-workout days.

\* \* \* \* \*

UNITED STATES PATENT AND TRADEMARK OFFICE
CERTIFICATE OF CORRECTION

| | |
|---|---|
| PATENT NO. | : 7,749,547 B2 |
| APPLICATION NO. | : 11/522266 |
| DATED | : July 6, 2010 |
| INVENTOR(S) | : Marvin A. Heuer et al. |

It is certified that error appears in the above-identified patent and that said Letters Patent is hereby corrected as shown below:

ON THE TITLE PAGE - REFERENCES CITED (56)

Foreign Patent Documents, "07252148 A" should read --7-252148 A--;
    Other Publications, "Latha et al., Effect of an aqueous extract of *Scoparia dulcis* on blood glucose, plasma insulin and some polyol pathway enzymes in experimental rat diabetes, Brazilian Journal of Medical and Biological Research 37: 577-586, 2004.*" ($2^{nd}$ occurrence) should be deleted; and
    Other Publications, under Ribnicky et al., "For" should read --for--.

ON TITLE PAGE AT (57) ABSTRACT

Line 1, "Creatine, Taurine" should read --creatine, taurine--;
    Line 2, "Phosphate." should read --phosphate.--;
    Line 3, "Double Fermented Triticum aestivum, Dextrose," should read --double-fermented *Triticum aestivum*, dextrose,--;
    Line 4, "Isomalt, Trehalose, D-Mannose," should read --isomalt, trehalose, D-mannose,--;
    Line 6, "Chromium, Glutamine and Alpha" should read --chromium, glutamine and alpha--;
    Line 7, "Lipoic Acid" should read --lipoic acid--; and
    Line 8, "Creatine" should read --creatine--.

COLUMN 5

Line 2, "cross sectional" should read --cross-sectional--.

COLUMN 9

Line 25, "mulberry" should be deleted.

Signed and Sealed this
Twenty-fifth Day of January, 2011

David J. Kappos
*Director of the United States Patent and Trademark Office*

CERTIFICATE OF CORRECTION (continued)
U.S. Pat. No. 7,749,547 B2

COLUMN 12

Line 23, "used" should be deleted.

COLUMN 14

Line 26, "is" should read --are--.

COLUMN 16

Line 5, "example." should read --examples.--;
Line 16, "and" should read --an--; and
Line 48, "Tarragon extract," should read --Tarragon,--.

COLUMN 17

Line 9, "and" should read --an--;
Line 21, "thereof," should read --thereof;--;
Line 27, "Creatine" should read --creatine-- and "Creatinol-O" should read --creatinol-O--;
Line 28, "Phosphate" should read --phosphate--;
Line 29, "Taurine" should read --taurine--;
Line 33, "Dipotassium Phosphate, Disodium Phosphate or Mangne-" should
  read --dipotassium phosphate, disodium phosphate or mangne- --;
Line 34, "Phosphate" should read --phosphate--;
Line 39, "Alpha Lipoic Acid" should read --alpha lipoic acid--;
Line 40, "Chromium." should read --chromium.--;
Line 42, "Glutamine" should read --glutamine--;
Line 53, "Trehalose." should read --trehalose.--;
Line 54, "Creatine" should read --creatine--; and
Line 55, "Creatinol-O-Phosphate" should read --creatinol-O-phosphate--.

COLUMN 18

Line 1, "Taurine" should read --taurine--;
Line 3, "Dipo-" should read --dipo- --;
Line 4, "Phosphate, Diosodium Phosphate or Magnesium" should read
  --phosphate, diosodium phosphate or magnesium--;
Line 5, "Phosphate" should read --phosphate--;
Line 9, "Trehalose" should read --trehalose--;
Line 16, "Alpha" should read --alpha--;
Line 17, "Lipoic Acid" should read --lipoic acid--;
Line 18, "Alpha" should read --alpha--;
Line 19, "Lipoic Acid" should read --lipoic acid--;
Line 21, "Creatine" should read --creatine--;

CERTIFICATE OF CORRECTION (continued)
U.S. Pat. No. 7,749,547 B2

Line 22, "Creatinol-O-Phosphate" should read --creatinol-O-phosphate--;
Line 23, "Taurine;" should read --taurine;--;
Line 24, "Dipotassium Phosphate, Disodium Phos-" should read --dipotassium phosphate, disodium phos--;
Line 25, "Magnesium Phosphate;" should read --magnesium phosphate;--;
Line 26, "Dextrose;" should read --dextrose;--;
Line 27, "Trehalose;" should read --trehalose;--;
Line 33, "Tarrigon" should read --tarrigon--;
Line 35, "Chromium Polynicotinate;" should read --chromium polynicotinate;--;
Line 36, "Glutamine;" should read --glutamine;--;
Line 37, "Alpha Lipoic Acid." should read --alpha lipoic acid.--;
Line 38, "1, 2, 3" should read --1-3--;
Line 39, "15, 13,14," should read --13-15,--;
Line 42, "double fermented" should read --double-fermented--;
Line 46, "claims 1, 2, 3, 13-15, 4-7," should read --claims 1-15.--; and
Line 47, "8, or 9-12." should be deleted.